United States Patent [19]

Baker et al.

[11] Patent Number: 5,177,084
[45] Date of Patent: Jan. 5, 1993

[54] THERAPEUTIC USE OF SUBSTITUTED BENZENES, FORMULATIONS THEREOF AND NOVEL SUBSTITUTED BENZENES

[75] Inventors: Raymond Baker, Much Hadam; Graham A. Showell, Welwyn Garden City, both of England

[73] Assignee: Merck Sharp & Dohme Ltd., Hertfordshire, England

[21] Appl. No.: 795,291

[22] Filed: Nov. 19, 1991

Related U.S. Application Data

[63] Continuation of Ser. No. 564,494, Aug. 8, 1990, abandoned.

[30] Foreign Application Priority Data

Aug. 8, 1989 [GB] United Kingdom ............... 8918061

[51] Int. Cl.⁵ ............................................. A61K 31/41
[52] U.S. Cl. ................................................... 514/305
[58] Field of Search ................ 546/133, 137; 514/305

[56] References Cited

FOREIGN PATENT DOCUMENTS 239309 9/1987 European Pat. Off. .
327155 8/1989 European Pat. Off. .

OTHER PUBLICATIONS

J. Med. Chem. (1981) 24 1475–82.
Helv. Chim. Acta. (1957) 40, 2170.

*Primary Examiner*—Marianne M. Cintins
*Assistant Examiner*—Catherine Scalzo
*Attorney, Agent, or Firm*—Manfred Polk; Charles Caruso

[57] ABSTRACT

Benzenes, substituted by a non-aromatic, non-fused 1-azabicycle and a substituent of low lipophilicity or a hydrocarbon substituent, their salts and prodrugs are useful in medicine, for example, in treating dementia. Some formulations of such benzenes are novel as are some of the compounds per se. They can be synthesized by methods analogous to those known in the art.

2 Claims, No Drawings

THERAPEUTIC USE OF SUBSTITUTED BENZENES, FORMULATIONS THEREOF AND NOVEL SUBSTITUTED BENZENES

CROSS REFERENCE TO RELATED APPLICATIONS

This is a continuation of application Ser. No. 564,494 filed on Aug. 8, 1990, now abandoned.

The present invention relates to a class of substituted benzene compounds which stimulate central muscarinic acetylcholine receptors and therefore are useful in the treatment of neurological and mental illnesses whose clinical manifestations are due to cholinergic deficiency. Such diseases include presenile and senile dementia (also known as Alzheimer's disease and senile dementia of the Alzheimer type respectively), Huntingdon's chorea, tardive dyskinesia, hyperkinesia, mania and Tourette Syndrome. Alzheimer's disease, the most common dementing illness, is a slowly progressive neurological disorder characterised by marked deficits in cognitive functions including memory, attention, language and visual perception capabilities.

Published European Patent Application No. 239039 discloses a class of oxadiazole compounds having a substituent of low lipophilicity, which are useful in the treatment of neurodegenerative disorders. In J. Med. Chem. (1981), 24 (12), 1475–82 is disclosed 3-hydroxy-3-(3-methoxyphenyl)quninuclidine and in Helv. Chim. Acta (1957), 40, 2170 is disclosed 3-(4-methoxyphenyl) quinuclidine. No therapeutic activity is ascribed to either compound. In Khim-Farm. Zh. (1982), 16 (3), 307–311 are disclosed 3-hydroxy-3-(4-methoxyphenyl)-quinuclidine; 3-hydroxy-3-(2-methoxyphenyl)quinuclidine and 3-(4-chlorophenyl)-3-hydroxy quinuclidine; the authors describe how these compounds did not display pharmacological activity. Indeed, as reported in the J. Med. Chem. article mentioned above, related compounds were tested for dopaminergic activity and found to be essentially inactive.

It was therefore unexpected to find that a class of benzene compounds do exhibit therapeutic activity and have been found to stimulate cholinergic transmission.

It is possible that the enhancement of cholinergic transmission demonstrated by the compounds according to this invention is achieved either directly by stimulating postsynaptic receptors, or indirectly by potentiating acetylcholine release.

The compounds according to the present invention are benzene, substituted on one of the ring carbon atoms thereof with a non-aromatic, non-hereof with a non-aromatic, non-fused 1-azabicyclic ring system and independently substituted on each of the other ring carbon atoms with a substituent of low lipophilicity or a hydrocarbon substituent provided that at least one such substituent contains a heteroatom and further provided that such substituent is other than hydroxy; and salts and prodrugs thereof. Examples of suitable heteroatoms are O,N,S and halo (eg. F, Cl, Br).

Accordingly, the present invention provides the therapeutic use of a compound of formula (I):

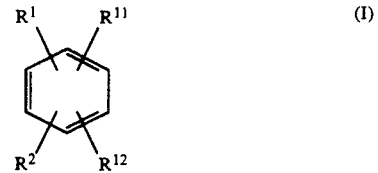

or a salt or prodrug thereof; wherein $R^1$ represents a non-aromatic, non-fused 1-azabicyclic ring system; and $R^2$, $R^{11}$ and $R^{12}$ independently represent hydrogen, halo, —$CF_3$, —$OR^6$, —$NR^6R^7$, —$NHOR^6$, —$NHNH_2$, —CN, $COR^8$, or a substituted or unsubstituted, saturated or unsaturated hydrocarbon group, provided that at least one of $R^2$, $R^{11}$ and $R^{12}$ is other than hydrogen or a hydrocarbon group, or $R^2$ and $R^{11}$ or $R^{12}$ taken together form a $C_{1-6}$ alkylenedioxy ring, wherein $R^6$ is $C_{1-6}$ alkyl, $C_{2-6}$ alkenyl or $C_{2-6}$ alkynyl, $R^7$ is hydrogen, $C_{1-6}$ alkyl or —$COCH_3$, and $R^8$ represents OH, —$OR^6$, $NHR^7$ or —$NR^6R^7$.

The present invention also provides a pharmaceutical composition comprising a compound of formula (I) as defined above or a pharmaceutically acceptable salt or prodrug thereof and a pharmaceutically acceptable carrier therefor other than wherein the compound of formula (I) is 3-hydroxy-3-(4-methoxyphenyl)-quinuclidine; 3-hydroxy-3-(2-methyoxyphenyl)quinuclidine or 3-(4-chlorophenyl)-3-hydroxy quinuclidine.

The present invention also provides a novel compound of formula (I) as defined above or a salt or prodrug thereof provided that when $R^1$ is optionally substituted 1-azabicyclo[2.2.1]heptanyl, 1-azabicyclo[3.3.1]heptanyl or 1-azabicyclo[2.2.2]octanyl, then at least two of $R^2$, $R^{11}$ and $R^{12}$ are other than hydrogen with the exception of 3-(2-chlorophenyl)-3-hydroxyquinuclidine;
3-(3-methoxyphenyl)quinuclidine;
3-3(3-trifluoromethylphenyl)quinuclidine;
3-(3-trifluoromethylphenyl)quinuclidine;
3-(3-chlorophenyl)-3-hydroxyquinuclidine;
3-hydroxy-3-(3-methoxyphenyl)-1-azabicyclo[2.2.1]heptane;
3-(3-halophenyl)quinuclidines; and
3-(3-methoxyphenyl)-1-azabicyclo[2.2.1]heptane.

In formula (I), preferably, $R^2$, $R^{11}$ and $R^{12}$ are each independently selected from hydrogen, halo (F, Cl, Br, I) and $OR^6$ provided that at least one of $R^2$, $R^{11}$ and $R^{12}$ is other than hydrogen. More preferably, $R^6$ is selected from $C_{1-6}$ alkyl and $C_{2-6}$ alkenyl and $R^7$ is $C_{1-6}$ alkyl.

The azabicyclic ring system is a non-aromatic ring system containing one nitrogen atom as the sole heteroatom. Suitably, the ring system contains up to 10 ring atoms, preferably up to 8 ring atoms. Preferably, the ring system contains a tertiary amino nitrogen atom in a caged structure. The bicyclic systems may be spiro or bridged. Preferably, the nitrogen atom is at a bridgehead. Examples of suitable ring systems for the group $R^1$ include the following:

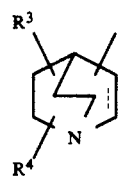

-continued

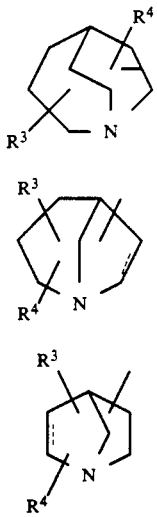

wherein the broken line represents an optional chemical bond; and the substituents $R^3$ and $R^4$ may be present at any position, including the point of attachment to the benzene ring, and independently represent hydrogen, $C_{1-4}$ alkyl, halo, $C_{1-4}$ alkoxy, hydroxy, carboxy or $C_{1-4}$ alkoxycarbonyl, or $R^3$ and $R^4$ together represent carbonyl.

Any substituent on the nitrogen atom of the azabicycle (designated $R^5$) is hydrogen or $C_{1-4}$ alkyl.

It will be appreciated that the nitrogen atom in the azabicyclic ring will carry a lone pair of electrons.

Suitably, the group $R^3$ is hydrogen or methyl; and $R^4$ is hydrogen, $C_{1-4}$ alkoxy, $C_{1-4}$ alkyl, $C_{1-4}$ alkoxycarbonyl, halo or hydroxy; preferably methoxy, methyl, fluoro, chloro, hydroxy or methoxycarbonyl. Preferably, one or both of $R^3$ and $R^4$ is hydrogen. More preferably, $R^4$ is hydroxy or hydrogen when $R^3$ is hydrogen.

Preferably, the group $R^5$ represents hydrogen or methyl.

Suitably, the azabicyclic ring system is azanorbornane, quinuclidine, 1-azabicyclo[2.2.2]octene (dehydroquinuclidine) or 1-azabicyclo[3.2.1]octane, any of which may in particular be either unsubstiuted or substituted with methyl, hydroxy, flouro, chloro or methoxycarbonyl. Preferably, $R^1$ is quinuclidine, 2,3-(dehydro)-quinuclidine, 1-azabicyclo[2.2.1]heptane or 1-azabicyclo[3.2.1]heptane, especially quinuclidine or 2,3-(dehydro)quinuclidine, optionally substituted with hydroxy.

When the groups $R^2$, $R^{11}$ and/or $R^{12}$ are hydrocarbon substituents, they may be $C_{1-15}$ alkyl, $C_{2-15}$ alkenyl, $C_{2-15}$ alkynyl, aryl or aralkyl. The alkyl, alkenyl or alkynyl groups may be straight, branched or cyclic groups. Suitably, the alkyl group comprises from 1 to 6 carbon atoms. The hydrocarbon group(s) may carry one or more substituents. Suitable substituent groups include halo, —$OR^6$, —$CF^3$, —$NR^6R^7$, —$NO^2$, optionally substituted aryl, keto, —$SR^6$, —$SOR^6$, —$SO^2R^6$, —$CO^2R^6$ and —$CONR^6R^7$; wherein $R^6$ and $R^7$ are as defined with respect to formula (I) above.

Substituents most suitable for the aryl group include chloro, bromo, methoxy, $C_{1-6}$ alkyl, methoxycarbonyl, trifluoromethyl, nitro and —$NR^6R^7$.

Preferably, the groups $R^2$, $R^{11}$ and $R^{12}$ independently represent hydrogen, halo, —$CF_3$, —$OR_6$, —$NHR^6$, —$CN$, —$COR^8$, phenyl($C_{1-3}$) alkyl, $C_{3-6}$ cycloalkyl, adamantyl, $C_{2-6}$ alkenyl, $C_{2-6}$ alkynyl, $C_{1-6}$ alkyl, or $C_{1-6}$ alkyl substituted with —$OR^6$, —$NHR^6$, —$SR^6$, —$CO_2R^6$, —$CON(R^6)_2$ or halo. Particular values of the groups $R^2$, $R^{11}$ and/or $R^{12}$ are hydrogen, chloro, fluoro, bromo, methyl, ethyl, isopropyl, cyclopropyl, benzyl, adamantyl, amino, dimethylamino, methoxy, ethoxy, isopropoxy, n-butoxy, allyloxy, propargyloxy, methyoxycarbonyl and ethoxycarbonyl. Particularly preferred values are methoxy, chloro and $CF_3$, especially methoxy and chloro for $R^2$ when $R^{11}$ and $R^{12}$ are each hydrogen. Suitably, $R^2$ and $R^{11}$ may be the same when $R^{12}$ is hydrogen.

A particularly preferred subclass of compounds of formula (I) or salts or prodrugs thereof are those wherein:

$R^1$ is a 7- or 8-membered, non aromatic, non-fused, 1-azabicycle, optionally substituted by hydroxy; $R^2$, $R^{11}$ and $R^{12}$ are each independently selected from hydrogen, halo (especially chloro), —$CF_3$, —$OR^6$ (especially —$OCH_3$), or $R^2$ and $R^{11}$ or $R^{12}$ taken together form a $C_{1-6}$ alkylenedioxy ring (especially 3,4-methylenedioxy or 3,4-ethylenedioxy).

Especially preferred is wherein:

$R^1$ is 1-azabicyclo[2.2.2]octanyl, 2,3-dehydro-1-azabicyclo[2.2.2]octanyl, 1-azabicyclo[3.2.1]octanyl, 2,3-dehydro-1-azabicyclo[3.2.1]octanyl, 1-azabicyclo[2.2.1]heptanyl and 2,3-dehydro-1-azabicyclo[2.2.1]heptanyl, each of which may be optionally substituted by hydroxy.

Most of the compounds of this invention have at least one asymmetric centre and often more than one; and can therefore exist both as enantiomers and as diastereoisomers. In particular, those compounds possessing an unsymmetrical azabicyclic ring system may exist as exo and endo diastereoisomers. It is to be understood that the invention covers all such isomers and mixtures thereof.

One group of prodrugs of compounds of this invention have a substituent on the benzene ring which is hydrolysable in vivo to an amino group.

Groups which are hydrolyzable in vivo to an amino group on the compounds of this invention may be readily ascertained by administering the compound to a human or animal and detecting, by conventional analytical techniques, the presence of the corresponding compound having an amino substituent in the urine of the human or animal. Examples of such groups include, for example, amido and urethane substituents, in particular a group of formula —NH.Q, wherein Q represents CHO, COR or $CO_2R$, and R represents an optionally substituted hydrocarbon group.

In this context, the hydrocarbon group R includes groups having up to 20 carbon atoms, suitably up to 10 carbon atoms, conveniently up to 6 carbon atoms. Suitable groups R include $C_{1-9}$ alkyl, $C_{2-6}$ alkenyl, $C_{2-6}$ alkynyl, $C_{3-7}$ cycloalkyl, $C_{3-7}$ cyclalkyl($C_{1-6}$)alkyl, aryl and aryl($C_{1-6}$)alkyl. The alkyl group R may be straight or branched chain and may contain, for example, up to 12 carbon atoms, suitable form 1 to 6 carbon atoms. In particular, the group may be substituted methyl, ethyl, n- or iso-propyl, n-, sec-, iso- or tert-butyl, n-or iso-heptyl, or n- or iso-octyl. Suitable cycloalkyl groups include cyclopentyl and cyclohexyl. The aryl group R includes phenyl and naphthyl optionally substituted with up to five, preferably up to three, substituent groups.

Also included within the scope of the present invention are salts of the novel compounds. It will be appreciated that salts of the compounds for use in medicine will be non-toxic, pharmaceutically acceptable salts. Other salts may, however, be useful for the preparation of the compounds of the invention or their non-toxic, pharmaceutically acceptable salts. Acid addition salts, for example, may be formed by mixing a solution of the compound with a solution of a pharmaceutically acceptable, non-toxic acid such as hydrochloric acid, oxalic acid, fumaric acid, maleic acid, succinic acid, acetic acid, citric acid, tartaric acid, carbonic acid or phosphoric acid. Preferred acid addition salts are the hydrogen oxalate, hydrochloride, sesquioxalate, hydrogen maleate, oxalate and hydrogen tartrate salts. Where the compound (I) carries a carboxylic acid group, the invention also contemplates salts thereof, preferably non-toxic, pharmaceutically acceptable salts thereof, such as the sodium, potassium and calcium salts thereof.

Salts of amine groups may also comprise the quaternary ammonium salts in which the amino nitrogen atom carries an alkyl, alkenyl, alkynyl or aralkyl group. Such quaternary ammonium derivatives penetrate poorly into the central nervous system and are therefore useful as peripherally selective muscarinic agents, useful for example as antispasmodic agents, agents to reduce gastric acid secretion, agents to block the muscarinic actions of acetylcholinesterase inhibitors in the treatment of myasthenia gravis and as agents to co-administer with muscarinic agonists in Alzheimer's disease.

Specific compounds within the scope of the formula (I) are:
3-hydroxy-3-(3-methoxyphenyl)quinuclidine;
3-hydroxy-3-(4-methoxyphenyl)quinuclidine;
3-hydroxy-3-(2-methoxyphenyl)quinuclidine;
3-hydroxy-3-(4-chlorophenyl)quinuclidine;
3-(4-methoxyphenyl)quinuclidine;
3-(4-chlorophenyl)-2,3-dehydroquinuclidine;
3-(3-methoxyphenyl)-2,3-dehydroquinuclidine;
3-(3,4-dimethoxyphenyl)quinuclidine;
3-(2,4-dimethoxyphenyl)quinuclidine;
3-(2,5-dimethoxyphenyl)quinuclidine;
3-(3-methoxyphenyl)quinuclidine;
2,3-dehydro-3-(2-methoxyphenyl)quinuclidine;
3-(2-chlorophenyl)-3-hydroxyquinuclidine;
3-(2,4-dimethoxyphenyl)-3-hydroxyquinuclidine;
3-(2,5-dimethoxyphenyl)-3-hydroxyquinuclidine;
3-(3,4-dimethoxyphenyl)-3-hydroxyquinuclidine;
3-(2,4-ethylenedioxyphenyl)-3-hydroxyquinuclidine;
2,3-dehydro-3-(2,4-dimethoxyphenyl)quinuclidine;
2,3-dehydro-3-(2,5-dimethoxyphenyl)quinuclidine;
2,3-dehydro-3-(3,4-dimethoxyphenyl)quinuclidine;
2,3-dehydro-3-(3,4-ethylenedioxyphenyl)quinuclidine;
3-(3,4-ethylenedioxyphenyl)quinuclidine;
3-hydroxy-3-(3-trifluoromethylphenyl)quinuclidine;
2,3-dehydro-3-(3-trifluoromethylphenyl)quinuclidine;
3-(3-trifluoromethylphenyl)quinuclidine;
3-(3,5-dichlorophenyl)-3-hydroxyquinuclidine;
3-(3-chlorophenyl)-2,3-dehydroquinuclidine;
6-hydroxy-6-(3-methoxyphenyl)-1-azabicyclo[3.2.1]octane;
3-(2,3-dimethoxyphenyl)-3-hydroxyquinuclidine;
2,3-dehydro-3-(2,3-dimethoxyphenyl)quinuclidine;
6-(3-methoxyphenyl)-1-azabicyclo[3.2.1]oct-6-ene;
2,3-dehydro-3-(3,5-dichlorophenyl)quinuclidine;
3-(3-chlorophenyl)3-hydroxyquinuclidine;
endo- and exo-6-(3-methoxyphenyl)-1-azabicyclo[3.2.1]octane;
3-(2,3-dimethoxyphenyl)quinuclidine;
3-hydroxy-3-(3,4-methylenedioxyphenyl)quinuclidine;
3-(3,5-dichlorophenyl)quinuclidine;
3-(3,5-dimethoxyphenyl)-3-hydroxyquinuclidine;
2,3-dehydro-3-(3,5-dimethoxyphenyl)quinuclidine;
3-(3,5-dimethoxyphenyl)quinuclidine;
3-(3,5-bis-trifluoromethylphenyl)-3-hydroxyquinuclidine;
3-(3,5-bis-trifluoromethylphenyl)-2,3-dehydroquinuclidine;
3-(3,5-bis-trifluoromethylphenyl)quinuclidine;
2,3-dehydro-3-(3,4-methylenedioxyphenyl)quinuclidine;
3-hydroxy-3-(3-methoxyphenyl)-1-azabicyclo[2.1.1]heptane;
3-(3-methoxyphenyl)-1-azabicyclo[2.2.1]hept-2-ene;
endo-3-(3-methoxyphenyl)1-azabicyclo[2.2.1]heptane;
and salts and prodrugs thereof.

The method of treatment of this invention includes a method of treating Alzheimer's disease, senile dementia of the Alzheimer type, Huntingdon's chorea, tardive dyskinesia, hyperkinesia, mania or Tourette syndrome by the administration of a patient in need of such treatment of a pharmacologically effective amount of a compound of formula (I), or a salt or prodrug thereof.

In the method of treatment of this invention, preferably, when $R^1$ is 3-hydroxy-quinuclidin-3-yl, and $R^{11}$ and $R^{12}$ are hydrogen, then $R^2$ is o- or p-methoxy, or p-chloro.

This invention therefore provides a compound of formula (I) for therapeutic use, such as for use in treating dementia and/or any of the other conditions referred to above. Preferably, when $R^1$ is 3-hydroxyquinuclidin-3-yl, and $R^{11}$ and $R^{12}$ are hydrogen, preferably $R^2$ is other than o- or p-methoxy, or p-chloro.

It may, where appropriate, be advantageous, in order to reduce unwanted peripherally mediated side-effects, to incorporate into any composition a periphery acting cholinergic antagonist (or anti-muscarinic agent). Thus the compounds (I) may be administered together with a peripheral cholinergic antagonist such as N-methylscopolamine, N-methylatropine, propantheline, methantheline or glycopyrrolate.

The compounds (I) can be administered orally, parenterally or rectally at a daily dose of about 0.01 to 10 mg/kg of body weight, preferably about 0.1 to 1 mg/kg, and may be administered on a regimen of 1–4 times a day. When a cholinergic antagonist is administered, it is incorporated at its conventional dose.

This invention therefore also provides a pharmaceutical composition comprising a compound of formula (I) and a pharmaceutically acceptable carrier therefor.

In the pharmaceutical compositions or formulations of this invention, when $R^1$ is 3-hydroxyquinuclidin-3-yl, and $R^{11}$ and $R^{12}$ are hydrogen, then preferably $R^2$ is other than o- or p-methoxy, or p-chloro.

More preferably, in the compositions of this invention, when $R^1$ is quinuclidin-3-yl, and $R^{11}$ and $R^{12}$ are hydrogen, then $R^2$ is p-methoxy; and when $R^1$ is 3-hydroxy-quinuclidin-3-yl, and $R^{11}$ and $R^{12}$ are H, then $R^2$ is methoxy or p-chloro; and when $R^1$ is 1-azabicyclo[2.2.1]heptan-7-yl, and $R^{11}$ and $R^{12}$ are hydrogen, then $R^2$ is p-methoxy or p-chloro.

Preferably, when $R^1$ is quinuclidinyl, and $R^{11}$ and $R^{12}$ are hydrogen, then $R^2$ is methoxy or chloro.

The pharmaceutical formulations of this invention preferably are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound (I), or a nontoxic, pharmaceutically acceptable salt thereof. When referring to these preformulation compositions as homogeneous, it is meant that the active ingredient is dispersed evenly throughout the composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, cetyl alcohol and cellulose acetate.

The liquid forms in which the compositions of the present invention may be incorporated for administration orally or by injection include aqueous emulsions with edible oils such as cottonseed oil, sesame oil, coconut oil and peanut oil, as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinyl-pyrrolidone and gelatin.

The present invention further provides a process for preparing a pharmaceutical formulation according to the invention which process comprises bringing a compound of formula (I) into association with a carrier therefor such as by mixing.

The compounds of this invention wherein $R^3$ and $R^4$ are each other than hydroxy- or carboxy- substituted on the azabicycle at the point of attachment to the benzene ring may be prepared by a process which comprises the dehydroxylation or decarboxylation of a compound of formula (III) (which is a sub-class of the compounds of formlula (I)) or a slat thereof:

(III)

wherein V represents a benzene ring independently substituted on each of the remaining ring carbon atoms with a substituent of low lipophilicity and/or a hydrocarbon substituent as defined above; A represents with a substituent of low lipophilicity and/or a hydrocarbon substituent as defined above; A represents the residue of an azabicyclic ring as defined above; and B represents hydroxy or carboxy.

When the group B in compound (III) is hydroxy, it may be removed by chlorination and elimination or by dehydration to provide compounds of formula (I) wherein $R^1$ contains unsaturation at the point of attachment to the benzene ring. When it is desired to prepare a compound of formula (I) wherein $R^1$ contains saturation at the point of attachment to the benzene ring, the unsaturated compound of formula (I) may be hydrogenated using conventional methods. Dehydration may be accomplished by treatment with an acid, for example with trifluoroacetic acid. For example, chlorination and elimination may be affected by treatment with phosphorus oxychloride in the presence of triethylamine, or with thionyl chloride followed, where necessary, by DBN. The chloride or the unsaturated product may then be hydrogenated under conventional conditions, such as over 10% palladium/carbon in methanol. Alternatively, the compound (III) may be dehydroxylated by the use of thionyl chloride followed by treatment with tributylin hydride in a solvent such as tetrahydrofuran in the presence of a radical initiator such as azabisisobutyronitrile.

The compound of formula (III) where B is hydroxy may be prepared by reaction of a ketone compound of formula (IV) with a metal derivative of a benzene compound of formula (V):

wherein A and V are as defined above; and M represents a metal atom, for example magnesium. The metal derivative for instance may be prepared by reacting the corresponding halo-substituted benzene compound such as the Br- or I-substituted benzene compound with the metal.

When the group B in compound (III) is carboxy it may be removed by standard decarboxylation techniques such as heating in aqueous solution made to pH1 with hydrochloric acid.

The compounds of formula (III) where B represents carboxy may be prepared by reaction of a compound of formula (VI) with a compound of formula (VII):

where $R^1$ and V are as defined above, Hal represents halo, and W represents cyano, a carboxylic acid group or a derivative thereof which activates the adjacent position; and subsequently; where necessary, converting the group W to carboxy, preferably by hydrolysis.

Preferably, W represents an alkyl ester group such as methoxycarbonyl. Preferably, the halo group is iodo. The reaction between compounds (VI) and (VII) may be carried out in the presence of a strong base such as lithium diisopropylamide in a solvent such as tetrahydrofuran.

The azabicyclic moiety may be introduced into the molecules concerned by methods known from the art, in particular by methods analogous to those described in EP-A-0239309.

After any of the above described processes is complete, one substituent can be converted to another. For example, an amino group may be converted to chloro, or hydrazo, —NHNH$_2$, via the intermediacy of diazonium, (—N$_2$). Similarly, alkoxycarbonyl groups may be converted, via carboxy, to an amino substituent, —NH$_2$; and methoxy may be converted to hydroxy by treatment with concentrated hydrobromic acid; these groups may then be further converted to any value of R$^2$ defined above.

In any of the above reactions it may be necessary and/or desirable to protect any sensitive groups in the compounds. For example, if the reactants employed include amino, carboxy, keto, hydroxy or thiol groups, these may be protected in conventional manner. Thus, suitable protecting groups for hydroxy groups include silyl groups such as trimethylsilyl or t-butyldimethylsilyl, and etherifying groups such as tetrahydropyranyl; and for amino groups include benzyloxycarbonyl and t-butoxycarbonyl. Keto groups may be protected in the form of a ketal. Carboxy groups are preferably protected in a reduced form such as in the form of their corresponding protected alcohols, which may be subsequently oxidised to give the desired carboxy group. Thiol groups may be protected by disulphide formation, either with the thiol itself or with another thiol to form a mixed disulphide. The protecting groups may be The following Examples illustrate the preparation of compounds according to the invention. Each of the compounds of the Examples demonstrates an affinity for the muscarinic receptor, having an IC$_{50}$ (concentration required to displace 50% of specific [3H]-N-methylscopolamine binding from rat cortical membrane preparations) significantly lower than 100 μM. Penetrability into the central nervous system of compounds of this invention was assessed by a measurable displacement of radioligand binding using standard "ex-vivo" binding techniques (Ref:J. Neurosurg., 1985, 63, 589–592).

In the Examples, all temperatures are in °C.; THF is tetrahydrofuran; and ether is diethyl ether.

DESCRIPTIVE EXAMPLE 1

3-Hydroxy-3-(3-methoxyphenyl)quinuclidine Hydrogen Oxalate

A solution of 3-quinuclidinone (10.88 g, 0.087 mol) in anhydrous diethyl ether (40 mL) was added to a solution of 3-methoxyphenylmagneisum bromide [prepared from 3-bromoanisole (14.04 g, 0.07 ml), iodine (2 crystals) and magnesium (2.00 g, 0.0825 mol) in anhydrous diethyl ether (30 mL)] at 5° C. over 20 minutes. After 18 hours at room temperature a saturated aqueous solution of ammonium chloride (200 mL) was added. Glacial acetic acid was added to adjust the aqueous solution of pH7 then the aqueous was separated and washed with ethyl acetate (100 mL).

The aqueous solution was basified to pH 12 with 2 M sodium hydroxide solution then extracted with dichloromethane (5×200 mL). The combined organics were dried (sodium sulphate) then evaporated to give a cream solid which was triturated with diethyl ether (2×150 mL) to afford the title compound free base as a cream solid (8.00 g, 45%), m.p. 142° C.-145° C.

The hydrogen oxalate salt had mp 202° C.-204° C. (dec.) (propan-2-ol/diethyl ether). R$_f$=0.35 in dichloromethane/methanol (20:1) on alumina plates; $^1$H NMR (360 MHz, D$_2$O) δ 1.64-174 (1H, m), 1.92-2.03 (2H, m) and 2.40-2.48 (1H, m 5 and 8-CH$_2$); 2.65-2.67 (1H, m, 4-CH); 3.24-3.32 (2H, m) and 3.42-3.47 (2H, m, 6-CH$_2$ and 7-CH$_2$); 3.58 (1H, dd, J=2, 14 Hz, 2-CH); 3.87 (3H, s, OCH$_3$); 3.98 (1H, dd, J=14 Hz, 2-CH); 7.04 (1H, dd, J=2,8 Hz, Ar-H); 7.11 (1H, dd, J$_1$=J$_2$=2 Hz; Ar-H); 7.16 (1H, broad d, J=8 Hz, Ar-H); 7.45 (1H, dd, J$_1$=J$_2$=8 Hz; Ar-H); MS, m/z 233 for M$^+$ of free base, HRMS, Found; C, 61.58; H, 6.96; N, 5.10. C$_{14}$H$_{19}$O$_2$.0.75 C$_2$H$_2$O$_4$ requires C, 61.88; H, 6.87; N, 4.66%).

DESCRIPTIVE EXAMPLE 2

3-Hydroxy-3-(4-Methoxyphenyl)quinuclidine Hydrogen Oxalate

The title compound free base (7.7 g, 44%) was obtained as described for Example 1. The hydrogen oxalate salt had mp 117° C.-120° C. (acetone). R$_f$=0.33 in dichloromethane/methanol (20:1) on alumina plates; $^1$H NMR (360 MHz, D$_2$O) δ 1.63-1.72 (1H, m), 1.91-2.02 (2H, m) and 2.37-2.47 (1H, m 5 and 8-CH$_2$); 2.65-2.66 (1H, m, 4-CH); 3.20-3.32 (2H, m) and 3.34-3.44 (2H, m, 6-CH$_2$ and 7-CH$_2$); 3.57 (1H, dd, J=2, 14 Hz; 3.85 (3H, s, OCH$_3$); 3.97 (1H, dd, J=2, 14 Hz); 7.07 (2H, d, J=9 Hz, 2×Ar-H); 7.49 (2H, dd, J=9 Hz, 2×Ar-H); MS, mz 233 for M$^+$ of free base, HRMS, Found; M$^+$, 233.1411, C$_{14}$H$_{19}$NO$_2$ requires 233.1416. (Found: C, 58.43; H, 6.45; N, 4.31. C$_{14}$H$_{19}$NO$_2$. C$_2$H$_2$O$_4$.0.25 H$_2$O requires C, 58.62; H, 6.61; N, 4.27%).

DESCRIPTIVE EXAMPLE 3

3-Hydroxy-3-(2-methoxyphenyl)quinuclidine

A solution of 3-quinuclidinone (3.97 g, 31.7 mmol) in THF (15 mL) was added dropwise to a solution of 2-methoxyphenylmagneisum bromide [prepared from 2-bromoanisole (3.76 mL, 28.9 mmol), iodine (2 crystals) and magnesium (0.77 g, 31.7 mmol) in THF (10 mL)] cooled in an ice/water bath. After 3 h at room temperature a saturated aqueous solution of ammonium chloride (50 mL) was added. The resulting mixture (pH10) was diluted with H$_2$O (50 mL) and extracted with dichloromethane (4×50 mL). The combined organic extracts were washed with brine, dried over magnesium sulphate and evaporated to a light yellow oil. The crude product was purified by chromatography through silica-gel using dichloromethane/methanol/ammonia (89:10:1) as eluent to give the title compound as a colourless oil (1.02 g); $^1$H NMR (360 MHz, CDCl$_3$) δ 1.45-1.65 (3H, m), and 2.32 (1H, m, 5 and 8-CH$_2$), 2.44 (1H, br, OH); 2.46 (1H, m, 4-CH); 2.81 (2H, t, J=8 Hz) and 2.93 (1H, m) and 3.10 (1H, m 6 and 7-CH$_2$), 3.29 (1H, d, J=15 Hz, 2-CH), 3.40 (1H, d, J=15 Hz, 2-CH), 3.91 (3H, s, OME), 6.98 (2H, m, Ar-H), 7.27 (2H, m, Ar-H); m/z 233 (M$^+$).

DESCRIPTIVE EXAMPLE 4

3-(4-Chlorophenyl)-3-hydroxy quinuclidine Hydrogen Oxalate

The title compound free base (4.98 g, 31%) was obtained as described for Example 1. The hydrogen oxalate salt had mp 184° C.-187° C. (propane-2-ol/methanol). R$_f$=0.64 in dichloromethane/methanol (20:1) on alumina plates; $^1$H NMR (360 MHz, D$_2$O) δ 1.62-1.72 (1H, m), 1.93-2.02 (2H, m); 2.40-2.47 (1H, m 5-CH$_2$ and 8-CH$_2$); 2.64-2.66 (1H, m, 4-CH); 3.22-3.31 (2H, m) and 3.40-3.46 (2H, m, 6-CH$_2$ and 7-CH$_2$); 3.58 (1H, dd, J=2, 14 Hz, 2-CH); 3.95 (1H, d, J=14 Hz, 2-CH); 7.44-7.56 (4H, m, 4×Ar-H); MS, m/z 237 for M$^+$ of free base; HRMS, Found; M$^+$, 237.0921, C$_{13}$H$_{16}$ClNO requires M, 237.0920. (Found: C, 54.98;

H, 5.52; N, 4.20. $C_{13}H_{16}ClNO \cdot C_2H_2O_4$ requires C, 54.97; H, 5.54; N, 4.27%).

DESCRIPTIVE EXAMPLE 5

3-(4-Methoxyphenyl)quinuclidine Hydrogen Oxalate

Triethylsilane (3.8 mL, 0.024 mol) was added to a stirred solution of 3-hydroxy-3-(4-methoxyphenyl)-quinuclidine (1.0 g, 0.0048 mol, prepared as in Example 2) in trifluoroacetic acid (10 mL). After 20 hours at 50° C. the solution was cooled to 5° C. and basified to pH9 with saturated sodium hydrogen carbonate solution. The mixture was extracted with dichloromethane (3×100 mL), then the combined organics were dried (sodium sulphate) then evaporated to dryness. The crude product was purified by flash chromatography on silica using dichloromethane/methanol (20:1) to afford the title compound free base (0.86 g, 83%). The hydrogen oxalate salt had mp 104° C.-106° C. (acetone). $R_f$=0.77 in dichlormethane/methanol (20:1) on alumina plates; $^1$H NMR (360 MHz, $D_2O$) δ 1.75-1.87 (1H, m), 1.88-1.92 (1H, m) and 2.03-2.17 (2H, m, 5-$CH_2$ and 8-$CH_2$); 2.22-2.24 (1H, m, 4-CH); 3.29-3.63 (6H, m, 2-$CH_2$, 6-$CH_2$ and 7-$CH_2$); 3.70-3.79 (1H, m, 3-CH); 3.83 (3H, s, $OCH_3$); 7.03 (2H, d, J=9 Hz, 2×Ar-H); 7.34 (2H, d, J=9 Hz, 2×Ar-H); MS, m/z 217 for M+ of free base. (Found: C, 61.86; H, 61.86; H, 6.81; N, 4.50.$C_{14}H_{19}NO \cdot C_2H_2O_4 \cdot 0.25\ H_2O$ requires C, 61.62; H, 6.95; N, 4.49%).

EXAMPLE 6

3-(4-Chlorophenyl)-2,3-quinuclidine Hydrogen Oxalate

Triethylsilane (7.6 mL, 0.047 mol) was added to a stirred solution of 3-(4-chlorophenyl)-3-hydroxyquinuclidine (2.0 g, 0.0094 mol) in trifluoroacetic acid (20 mL) and dichloromethane (5 mL). After 20 hours at gentle reflux the reaction mixture was worked up as described for Example 5. The hydrogen oxalate salt had mp 131°-133° C. (propan-2-ol/diethyl ether). $R_f$0.29 in dichloromethane/methanol (20:1) on silica plates; $^1$H NMR (360 MHz, $D_2O$) δ 1.81-1.89 (2H, m), and 2.12-2.20 (2H, m, 5-$CH_2$ and 8-$CH_2$); 3.14-3.23 (2H, m) and 3.58-3.66 (3H, m, 4-CH, 6-$CH_2$ and 7-$CH_2$); 6.97 (1s, 2-CH); 7.43-7.59 (4H, m 4×Ar-H); MS, m/z 219 for M+ of free base. (Found: C, 57.68; H, 5.17; N, 4.45. $C_{13}H_{14}NCl \cdot C_2H_2O_4 \cdot 0.25\ H_2O$ requires C, 57.33; H, 5.29; N, 4.46%).

EXAMPLE 7

2,3-Dehydro-3-(3-methoxyphenyl)quinuclidine Hydrogen Oxalate

The title compound was prepared as described in Example 6, mp 76°-78° C. (propan-2-ol/diethyl ether). $R_f$=0.40 in dichloromethane/methanol (9:1) on silica; $^1$H NMR (360 MHz, $D_2O$) δ 1.83-1.91 (2H, m) and 2.12-2.21 (2H, m) and 3.58-3.66 (3H, m, 4-CH, 6-$CH_2$ and 7-$CH_2$); 3.87 (3H, s, $OCH_3$); 6.97 (1H, d, J=1 Hz, 2-CH); 7.09 (1H, dd, J=2, 8 Hz, Ar-H); 7.13 (1H, dd, $J_1$=$J_2$=2 Hz, Ar-H); 7.21 (1H, d, J=8 Hz, Ar-H); 7.45 (1H, dd, $J_1$=$J_2$=8 Hz, Ar-H). (Found: C, 62.26; H, 6.28; N, 4.50. $C_{14}H_{17}NO \cdot C_2H_2O_4 \cdot 0.25\ H_2O$ requires C, 62.03; H, 6.34; N, 4.52%).

EXAMPLE 8

2,3-Dehydro-3-(2-methoxyphenyl)quinuclidine Hydrogen Oxalate

Triethylsilane (1.18 mL, 7.36 mmol) was added to a stirred solution of 3-hydroxy-3-(2-methoxyphenyl)-quinuclidine (0.25 g, 0.94 mmol) in trifluoroacetic acid (1.3 mL) and dichloromethane (5 mL). After 18 h at room temperature the solution was evaporated and then dissolved in aqueous potassium carbonate solution (1 N, 50 mL) and extracted with dichloromethane (4×25 mL). The combined organic extracts were dried over magnesium sulphate, evaporated and the crude product purified by chromatography through silica-gel eluting with dichloromethane/methanol/ammonia (84.5:5:0.5) to give the free base as a colourless oil (0.19 g). The hydrogen oxalate salt had mp 128° C.-134° C. (methanol/diethyl/ether); $^1$H NMR (360 MHz, $D_2O$) δ 1.84-1.96 (2H, m) and 2.05-2.16 (2H, m, 5 and 8-$CH_2$); 3.23 (2H, m, 6-$CH_2$); 3.45 (1H, m, 4-CH); 3.60 (2H, m, 7-$CH_2$); 3.90 (3H, s, OMe); 6.89 (1H, s, 2-CH); 7.06-7.18 (2H, m, Ar-H); 7.35-7.56 (2H, m, Ar-H); m/z 215 (M+). (Found: C, 61.04; H, 6.28; N, 4.45. $C_{14}H_{17}NO \cdot C_2H_2O_4 \cdot 0.5\ H_2O$ requires C, 61.14; H, 6.41; N, 4.45%).

EXAMPLE 9

3-(2-Chlorophenyl)-3-hydroxyquinuclidine Hydrochloride

The title compound free base (0.94 g, 14%) was obtained as described for Example 1. The hydrochloride salt had mp 260°-265° C. (MeOH/$Et_2O$). $R_f$=0.60 in dichloromethane/methanol/ammonia (40:10:1) on silica plates; $^1$H NMR (360 MHz, $D_2O$) δ 1.95-2.09 (2H, m, 5-$CH_2$); 2.13-2.23 and 2.43-2.51 (each 1H, each m, 8-$CH_2$); 3.06-3.08 (1H, m, 4-CH); 3.17-3.50 (4H, m, 6-$CH_2$ and 7-$CH_2$); 3.80 (1H, dd, J=2, 14 Hz, one of 2-$CH_2$); 4.12 (1H, dd, J=2, 14 Hz, one of 2-$CH_2$); 7.33-7.43 and 7.55-7.60 (each 2H, each m, 4×Ar-H); MS, m/z 238 for (M+H)+ of free base. (Found: C, 56.36; H, 6.27; N, 4.96. $C_{13}H_{16}ClNO \cdot HCl \cdot 0.2\ H_2O$ requires C, 56.21; H, 6.31; N, 5.02%).

EXAMPLE 10

3-(3-Methoxyphenyl)quinuclidine Hydrogen Oxalate 2,3-Dehydro-3-(3-methoxyphenyl)quinuclidine (1.10 g, 0.0051 mol) was hydrogenated in ethanol (20 mL) containing 10% palladium on carbon (150 mg) and glacial acetic acid (0.3 mL, 0.0052 mol) at $3.5 \times 10^5$ N.m$^{-2}$ (50 psi). The reaction mixture was filtered, then evaporated to dryness. The resulting gum was dissolved in water (10 mL), basified to pH~10 with sodium carbonate and extracted with dichloromethane (5×10 mL). The combined organics were dried (sodium sulphate) then evaporated to provide the crude free base which was purified by column chromatography on silica by elution with dichloromethane/methanol (20:1). The required product was obtained as a pale yellow oil (200 mg). The hydrogen oxalate salt had mp 94°-96° C. (propan-2-ol/diethyl ether). $R_f$=0.77 in dichloromethane/methanol (20:1) on alumina plates; $^1$H NMR (360 MHz, $D_2O$) δ 1.74-2.22 (4H, m, 5-$CH_2$ and 8-$CH_2$); 2.28-2.30 (1H, m, 4-CH); 3.28-3.60 (6H, m, 2-$CH_2$, 6-$CH_2$ and 7-$CH_2$); 3.72-3.78 (1H, m, 3-CH); 3.85 (3H, s, $OCH_3$); 6.96 (1H, s, 2-aromatic H); 6.97 (1H, d, J=8 Hz, 4-aromatic H); 7.03 (1H, d, J=8 Hz, 6-aromatic H); 7.41 (1H, dd, $J_1$=$J_2$=8 Hz, 5-aromatic H); MS, m/z 217 for M+ of free base. (Found: C, 61.84; H, 6.82; N, 4.51. $C_{14}H_{19}NO \cdot C_2H_2O_4 \cdot 0.25\ H_2O$ requires C, 61.62; H, 6.95; N, 4.49%).

EXAMPLE 11

3-(2,4-Dimethoxyphenyl)-3-hydroxyquinuclidine Hydrogen Oxalate

'Butyllithium (100 mL of a 1.7 M solution in pentane) was added dropwise to a stirred, cooled (−78° C.) solution of 1-bromo-2,4-dimethoxybenzene (12.9 mL, 0.09 mol) in anhydrous diethyl ether (60 mL) under a nitrogen atmosphere, keeping the temperature below −65° C. After 1 hour at −78° C. a solution of 3-quinuclidine (10.0 g, 0.08 mol) in anhydrous diethyl ether (80 mL) was added dropwise, keeping the temperature below −65° C. After addition the reaction mixture was stirred whilst warming to room temperature for 16 hours. Saturated ammonium chloride solution (200 mL) was added followed by glacial acetic acid to pH=6. The aqueous layer was separated, washed with ethyl acetate (100 mL), then the aqueous was basified to pH = 12 with 2 M sodium hydroxide solution and extracted with dichloromethane (5×20 mL). The combined organics were dried (sodium sulphate) then evaporated to give a pale yellow gum (15.7 g) which was triturated with diethyl ether (200 mL) to afford the title compound free base as a colourless solid (9.55 g, 45%), mp 145°–148° C. The hydrogen oxalate salt had mp 125°–128° C. (acetone). $R_f$=0.15 in dichloromethane/methanol (5:1) on silica plates; $^1$H NMR (360 MHz, D$_2$O) δ 1.87–2.13 (3H, m) and 2.37–2.43 (1H, m, 5-CH$_2$ and 8-CH$_2$); 2.92–2.94 (1H, m, 4-CH); 3.12–3.42 (4H, m, 6-CH$_2$ and 7-CH$_2$); 3.63 (1H, d, J=12 Hz, one of 2-CH$_2$); 3.78 (1H, dd, J=2, 12 Hz, one of 2-CH$_2$); 3.85 (3H, s, OCH$_3$); 3.87 (3H, s OCH$_3$); 6.62 (1H, dd, J=2.5 9 Hz, 5-aromatic H); 6.72 (1H, d, J=2.5 Hz, 3-aromatic H); 7.32 (1H, d, J=9 Hz, 6-aromatic H); MS, Cl+, m/z 264 for (M+H)+ of free base. (Found: C, 57.78; H, 6.63; N, 4.02. C$_{15}$H$_{21}$NO$_3$.C$_2$H$_2$O$_4$ requires C, 57.78; H, 6.56; N, 3.96%).

EXAMPLE 12

3-(2,5-Dimethoxyphenyl)-3-hydroxyquinuclidine Hydrogen Oxalate

The title compound free base (7.50 g, 36%) was obtained from 3-quinuclidinone and 1-bromo-2,5-dimethoxybenzene as described for Example 11. The hydrogen oxalate salt had mp 138°–142° C. (propan-2-ol/diethyl ether). $R_f$=0.15 in dichloromethane/methanol (5:1) on silica plates; $^1$H NMR (360 MHz, D$_2$O) δ 1.92–2.15 (3H, m), and 2.38–2.44 (1H, m, 5-CH$_2$ and 8-CH$_2$); 2.93–2.94 (1H, m, 4-CH); 3.14–3.43 (4H, m, 6-CH$_2$ and 7-CH$_2$); 3.65 (1H, dd, J=14 Hz, one of 2-CH$_2$); 3.81 (3H, s, OCH$_3$); 3.84 (3H, s, OCH$_3$); 3.85 (1H, dd, J=2, 14 Hz, one of 2-CH$_2$); 6.98 (1H, d, J=3 Hz, 6-aromatic H); 7.03 (1H, dd, J=3, 9 Hz, 4-aromatic H); 7.11 (1H, d, J=9 Hz; 3-aromatic H); MS, m/z 263 for M+ of free base. (Found: C, 56.12; H, 6.44; N, 4.06. C$_{15}$H$_{21}$NO$_3$.C$_2$H$_2$O$_4$.0.5 H$_2$O requires C, 56.35; H, 6.67; N, 3.87%).

EXAMPLE 13

3-(3,4-Dimethoxyphenyl)-3-hydroxyquinuclidine Hydrogen Oxalate

The title compound free base (3.56 g, 17%) was obtained from 3-quinuclidinone and 1-bromo-3,4-dimethoxybenzene as described for Example 11. The hydrogen oxalate salt had mp 151°–152° C. (ethyl acetate). $R_f$=0.2 in dichloromethane/methanol (9:1) on silica plates; $^1$H NMR (360 MHz, D$_2$O) δ 1.70–1.73 (1H, m); 1.92–2.02 (2H, m) and 2.41–2.44 (1H, m, 5-CH$_2$ and 8-CH$_2$); 2.65–2.68 (1H, m, 4-CH); 3.24–3.34 (2H, m) and 3.41–3.46 (2H, m, 6-CH$_2$ and 7-CH$_2$); 3.56 (1H, dd, J=2, 14 Hz, one of 2-CH$_2$); 3.88 (3H, s, OCH$_3$); 3.89 (3H, s, OCH$_3$); 3.99 (1H, d, J=14 Hz, one of 2-CH$_2$); 7.01–7.14 (3H, m, 3×Ar-H); MS, m/z 264 for (M+H)+. (Found: C, 57.85; H, 6.64; N, 4.03. C$_{17}$H$_{21}$NO$_3$.C$_2$H$_2$O$_4$ requires C, 57.78; H, 6.56; N, 3.96%).

EXAMPLE 14

3-(3,4-Ethylenedioxyphenyl)-3-hydroxyquinuclidine Hydrogen Oxalate

The title compound free base (12.20 g, 47%) was obtained from 3-quinuclidinone and 3,4-ethylenedioxybromobenzene as described for Example 11. The hydrogen oxalate salt had mp 80°–83° C. (propan-2-ol). $R_f$=0.15 in dichloromethane/methanol (5:1) on silica plates; $^1$H NMR (360 MHz, D$_2$O) δ 1.63–1.72 (1H, m); 1.92–2.01 (2H, m) and 2.36–2.46 (1H, m, 5-CH$_2$ and 6-CH$_2$); 2.60–2.62 (1H, m, 4-CH); 3.21–3.32 (2H, m) and 3.37–3.45 (2H, m, 6-CH$_2$ and 7-CH$_2$); 3.53 (1H, dd, J=2, 14 Hz, one of 2-CH$_2$); 3.92 (1H, d, J=14 Hz, one of 2-CH$_2$); 4.32 (4H, s, 2×OCH$_2$); 6.94–7.07 (3H, m, 3×Ar-H); MS, m/z 261 for M+ of free base. (Found: C, 55.42; H, 6.37; N, 3.68. C$_{15}$H$_{19}$NO$_3$.C$_2$H$_2$O$_4$.H$_2$O. requires C, 55.28; H, 6.28; N, 3.79%).

EXAMPLE 15

2,3-Dehydro-3-(2,4-dimethoxyphenyl)quinuclidine Hydrogen Oxalate 3-(2,4-Dimethoxyphenyl)-3-hydroxyquinuclidine (8.5 g, 0.032 mol, prepared in Example 11) was heated under reflux in dichloromethane (25 mL) containing trifluoroacetic acid (25 mL) for 24 hours. The reaction mixture was evaporated to dryness and the residue dissolved in water (30 mL), basified to pH=12 with 2 M sodium hydroxide solution then extracted with dichloromethane (3×30 mL). The combined organics were dried (sodium sulphate) then evaporated to give a pale yellow gum which was purified by column chromatography on silica using dichloromethane/methanol (20:1). The title compound free base was obtained as a colourless gum (6.92 g, 88%). The hydrogen oxalate salt had mp 157°–158° C. (propan-2-ol/diethyl ether). $R_f$=0.20 in dichloromethane/methanol (9:1) on silica; $^1$H NMR (360 MHz, D$_2$O) δ 1.84–1.91 (2H, m) and 2.06–2.14 (2H, m, 5-CH$_2$ and 8-CH$_2$); 3.14–3.22 (2H, m) and 3.56–3.64 (2H, m, 6-CH$_2$ and 7-CH$_2$); 3.43–3.45 (1H, m, 4-CH); 3.87 (3H, s, OCH$_3$); 3.88 (3H, s, OCH$_3$); 6.67 (1H, dd, J=2.5 8 Hz, 5-aromatic H); 6.70 (1H, d, J=2.5 Hz, 3-aromatic H); 6.86 (1H, s, 2-CH); 7.33 (1H, d, J=8 Hz, 6-aromatic H); MS, m/z 245 for M+ of free base. (Found: C, 60.20; H, 6.27; N, 4.10. C$_{15}$H$_{19}$NO$_2$.C$_2$H$_2$O$_4$.0.25 H$_2$O requires C, 60.08; H, 6.38; N, 4.12%).

EXAMPLE 16

2,3-Dehydro-3-(2,5-dimethoxyphenyl)quinuclidine Sesquioxalate

The title compound free base (1.50 g, 27%) was obtained from 3-(2,5-dimethoxyphenyl)-3-hydroxyquinuclidine (as described in Example 12) by the method described in Example 15. The hydrogen oxalate salt had mp 108°–110° C. (propan-2-ol/diethyl ether). $R_f$=0.20 in dichloromethane/methanol (9:1) on silica plates; $^1$H NMR (360 MHz, D$_2$O) δ 1.89–1.96 (2H, m) and 2.07–2.15 (2H, m, 5-CH$_2$ and 8-CH$_2$); 3.16–3.24 (2H, m)

and 3.58–3.67 (2H, m, 5-CH$_2$ and 7-CH$_2$); 3.41–3.43 (1H, m, 4-CH); 3.82 (3H, s, OCH$_3$); 3.85 (3H, s, OCH$_3$); 6.90 (1H, s, 2-CH); 6.94 (1H, d, J=3 Hz, 6-aromatic H); 7.06 (1H, dd, J=3, 9 Hz, 4-aromatic-H); 7.11 (1H, d, J=9 Hz, 3-aromatic H); MS, m/z 245 for M+ of free base. (Found: C, 56.61; H, 5.98; N, 3.82. C$_{15}$H$_{19}$NO$_2$.1.5 C$_2$H$_2$O$_4$ requires C, 56.84; H, 5.83; N, 3.68%).

EXAMPLE 17

2,3-Dehydro-3-(3,4-Dimethoxyphenyl)quinuclidine Hydrogen Oxalate

The title compound free base (1.31 g, 49%) was obtained from 3-(3,4-dimethoxyphenyl)-3-hydroxyquinuclidine (as described in Example 13) by the method described in Example 15. The hydrogen oxalate salt had mp 154°–157° C. (propan-2-ol/diethyl ether). R$_f$=0.20 in dichloromethane/methanol (9:1) on silica plates; $^1$H NMR (360 MHz, D$_2$O) δ 1.83–1.89 (2H, m) and 2.13–2.21 (2H, m, 5-CH$_2$ and 8-CH$_2$); 3.16–3.23 (2H, m) and 3.59–3.69 (3H, m, 4-CH, 6-CH$_2$ and 7-CH$_2$); 3.89 (6H, s, 2×OCH$_3$); 6.92 (1H, s, 2-CH); 7.10 (1H, d, J=9 Hz, 5-aromatic H); 7.15 (1H, d, J=2 Hz, 2-aromatic H); 7.23 (1H, dd, J=2, 9 Hz, 6-aromatic H); MS, m/z 245 for M+ of free base. (Found: C, 59.70; H, 6.36; N, 4.10. C$_{15}$H$_{19}$NO$_2$.C$_2$H$_2$O$_4$0.30 H$_2$O requires C, 59.92; H, 6.39; N, 4.11%).

EXAMPLE 18

2,3-Dehydro-3-(3,4-ethylenedioxyphenyl)quinuclidine Hydrogen Oxalate

The title compound free base (6.0 g, 59%) was obtained from 3-(3,4-ethlenedioxyphenyl)-3-hydroxyquinuclidine (as described in Example 14) by the method described in Example 15. The hydrogen oxalate salt had mp 145°–148° C. (dec.) (propan-2-ol/diethyl ether). R$_f$=0.20 in dichloromethane/methanol (9:1) on silica plates; $^1$H NMR (360 MHz, D$_2$O) δ 1.84–1.90 (2H, m) and 2.15–2.22 (2H, m, 5-CH$_2$ and 8-CH$_2$); 3.16–3.25 (2H, m) and 3.55–3.69 (3H, m, 4-CH, 6-CH$_2$ and 7-CH$_2$); 4.37 (4H, s, 2×OCH$_2$); 6.92 (1H, s, 2-CH); 6.99–7.16 (3H, 3×aromatic-H); MS, m/z 243 for M+ of free base. (Found: C, 60.00; H, 6.11; N, 4.06. C$_{15}$H$_{17}$NO$_2$.C$_2$H$_2$O$_4$.0.5 H$_2$O requires C, 59.64; H, 5.89; N, 4.09%).

EXAMPLE 19

3-(2,4-Dimethoxyphenyl)quinuclidine Hydrogen Oxalate 2,3-Dehydro-3-(2,4-dimethoxyphenyl)quinuclidine (5.9 g, 0.024 mol, Example 15) was hydrogenated at 3.5×10$^5$ N.m$^{-2}$ (50 psi) in ethanol (40 mL) containing 10% palladium on carbon (0.59 g) and glacial acetic acid (1.5 mL, 0.024 mol). The reaction mixture was filtered, then evaporated to dryness. The residue was dissolved in water (30 mL), basified to pH∼12 with 2 M sodium hydroxide solution then extracted with dichloromethane (4×40 mL). The combined organics were dried (sodium sulphate), evaporated to dryness and the crude product purified by column chromatography on silica using dichloromethane/methanol (15:1) to afford the title compound free base (1.10 g, 19%) as a colourless gum. The hydrogen oxalate salt had mp 143° C. (propan-2-ol/diethyl ether). R$_f$=0.27 in dichloromethane/methanol (5:1) on silica plates; $^1$H NMR (360 MHz, D$_2$O) δ 1.78–2.14 (4H, m, 5-CH$_2$ and 8-CH$_2$); 2.25–2.27 (1H, m, 4-CH); 3.24–3.42 (5H, m, one of 2-CH$_2$, 6-CH$_2$ and 7-CH$_2$); 3.60–3.66 (1H, m, 3-CH); 3.72–3.79 (1H, one of 2-CH$_2$); 3.84 (6H, s, 2×OCH$_3$); 6.66 (1H, dd, J=2, 8 Hz, 5-aromatic H); 6.69 (1H, d, J=2 Hz, 3-aromatic H); 7.29 (1H, d, J=8 Hz, 6-aromatic H); MS, m/z 247 for M+ of free base. (Found: C, 58.20; H, 7.01; N, 4.22. C$_{15}$H$_{21}$NO$_2$.C$_2$H$_2$O$_4$.0.75 H$_2$O requires C, 58.19; H, 7.04; N, 3.99%).

EXAMPLE 20

3-(2,5-Dimethoxyphenyl)quinuclidine Hydrogen Oxalate 2,3-Dehydro-3-(2,5-dimethoxyphenyl)quinuclidine (1.6 g, 0.0051 mol, Example 16) was hydrogenated in ethanol (35 mL) containing 10% palladium on carbon (0.14 g) at 3.15×10$^5$ N.m$^{-2}$ (45 psi). The reaction mixture was filtered then evaporated to dryness. The crude product was purified by column chromatography on silica using dichloromethane/methanol (20:1) to give the title compound free base (0.81 g, 64%) as a colourless oil. The hydrogen oxalate salt had mp 88°–92° C. (propan-2-ol/diethyl ether). R$_f$=0.25 in dichloromethane/methanol (5:1) on silica plates; $^1$H NMR (360 MHz, D$_2$O) δ 1.80–1.89 (1H, m) and 1.95–2.16 (3H, m, 5-CH$_2$ and 8-CH$_2$); 2.30–2.32 (1H, m, 4-CH); 3.25–3.45 (5H, m, one of 2-CH$_2$, 6-CH$_2$ and 7-CH$_2$); 3.67–3.73 (1H, m, 3-CH); 3.75–3.82 (1H, m, one of 2-CH$_2$), 3.83 (6H, s, 2×OCH$_3$); 6.94–6.99 (2H, m, 4 and 6-aromatic H); 7.07 (1H, d, J=9 Hz, 3-aromatic H); MS, m/z 247 for M+ of free base. (Found: C, 58.37; H, 7.04; N, 4.25. C$_{15}$H$_{21}$NO$_2$.C$_2$H$_2$O$_4$.0.75 H$_2$O requires C, 58.19; H, 7.04; N, 3.99%).

EXAMPLE 21

3-(3,4-Dimethoxyphenyl)quinuclidine Hydrogen Oxalate 2,3-Dehydro-3-(3,4-dimethoxyphenyl)quinuclidine (0.67 g, 0.0027 mol, Example 17) was hydrogenated in ethanol (30 mL) containing 10% palladium on carbon (0.10 g) at atmospheric pressure. The reaction mixture was filtered then evaporated to dryness. The crude product was purified by column chromatography on silica using dichloromethane/methanol (10:1) to afford the title compound free base. The hydrogen oxalate salt had mp 134°–136° C. (propan-2-ol/diethyl ether). R$_f$=0.14 in dichloromethane/methanol (5:1) on silica plates; $^1$H NMR (360 MHz, D$_2$O) δ 1.70–1.94 (2H, m) and 2.07–2.14 (2H, m, 5-CH$_2$ and 8-CH$_2$); 2.26–2.28 (1H, m, 4-CH); 3.27–3.59 (6H, m, one of 2-CH$_2$, 3-CH, 6-CH$_2$ and 7-CH$_2$); 3.71–3.78 (1H, m, one of 2-CH$_2$); 3.87 (3H, s, OCH$_3$); 3.88 (3s, OCH$_3$); 6.99–7.03 (2H, m, 2-aromatic H and 6-aromatic H); 7.90 (1H, d, J=8 Hz, 5-aromatic H); MS, m/z 248 for (M+H)+ of free base. (Found: C, 57.38; H, 6.90; N, 4.23. C$_{15}$H$_{21}$NO$_2$.C$_2$H$_2$O$_4$H$_2$O requires C, 57.45; H, 7.09; N, 3.94%).

EXAMPLE 22

3-(3,4-Ethylenedioxyphenyl)quinuclidine Hydrogen Maleate 2,3-Dehydro-3-(3,4-ethylendioxyphenyl)quinuclidine (5.00 g, 0.0206 mol, Example 18) was hydrogenated in ethanol (50 mL) containing 10% palladium on carbon (0.50 g) at 2.07×10$^5$ N.m$^{-2}$ (30 psi). The reaction mixture was filtered than evaporated to dryness. The crude product was purified by column chromatography on silica using dichloromethane/methanol (20:1) to give the title compound free base (2.86 g, 58%) as a pale yellow gum. The hydrogen maleate salt gave a hygroscopic glass. R$_f$=0.22 in dichloromethane/methanol (5:1) on silica plates; $^1$H NMR (360 MHz, D$_2$O) δ 1.75–1.87 (1H, m) and 2.04–2.17 (2H, m, 5-CH$_2$ and 8-CH$_2$); 2.19–2.22 (1H, m, 4-CH); 3.26–3.52 (6H, m, one of 2-CH$_2$, 3-CH, 6-CH$_2$ and 7-CH$_2$); 3.64–3.75 (1H, m, one of 2-CH$_2$); 4.30 (4H, s, 2×OCH$_2$); 6.35 (1.7H, s, maleic acid protons); 6.87–6.96 (3H, m, 3×aromatic-H); MS, m/z 245 for M+ of free base. (Found: C, 57.78; H, 6.46; N, 3.76. C$_{15}$H$_{19}$NO$_2$.0.85 C$_4$H$_4$.2 H$_2$O requires C, 58.16; H, 7.00; N, 3.69%).

EXAMPLE 23

3-Hydroxy-3-(3-trifluoromethylphenyl)quinuclidine Hydrogen Oxalate

The title compound free base (2.78 g, 13%) was obtained from 3-quinuclidine and 3-bromobenzotrifluoride as described for Example 11. The hydrogen oxalate salt had mp 244° C. (dec.) (propan-2-ol/methanol). R$_f$=0.23 in dichloromethane/methanol (5:1) on silica plates; $^1$H NMR (360 MHz, D$_2$O) δ 1.63–1.72 (1H, m) 1.95–2.05 (2H, m) and 2.43–2.51 (1H, m, 5-CH$_2$ and 8-CH$_2$); 2.71–2.72 (1H, m, 4-CH); 3.25–3.38 (2H, m) and 3.44–3.49 (2H, m, 6-CH$_2$ and 7-CH$_2$); 3.63 (1H, dd, J=2, 14 Hz, one of 2-CH$_2$); 4.02 (1H, d=14 Hz, one of 2-CH$_2$); 7.63–7.86 (4H, m, 4×Ar-H); MS, m/z 271 for M+ of free base. (Found: C, 54.73; H, 5.28; N, 4.20. C$_{14}$H$_{16}$NO.0.75 C$_2$H$_2$O$_4$ requires C, 54.95; H, 5.21; N, 4.13%).

EXAMPLE 24

2,3-Dehydro-3-(3-trifluoromethylphenyl)quinuclidine Hydrogen Oxalate

The title compound free base (1.45 g, 60%)oxy-3-(3-trifluormethylphenyl)quinuclidine (as described in Example 23) by the method described in Example 15, except that the reaction mixture was heated at reflux for 60 hours. The hydrogen oxalate salt had mp 132°–133° C. (propan-2-ol/methanol). R$_f$=0.35 in dichloromethane/methanol (5:1) on silica plates; $^1$H NMR (360 MHz, D$_2$O) δ 1.85–1.93 (2H, m) and 2.14–2.23 (2H, m, 5-CH$_2$ and 8-CH$_2$); 3.17–3.26 (2H, m) and 3.61–3.69 (3H, m, 4-CH, 6-CH$_2$ and 7-CH$_2$); 7.06 (1H, d, J=1.5 Hz, 2-CH); 7.62–7.89 (4H, m, 4×Ar-H); MS, m/z 253 for M+ of free base. (Found: C, 55.78; H, 4.78; N, 4.03. C$_{14}$H$_{14}$F$_3$N.C$_2$H$_2$O$_4$ requires C, 55.98; H, 4.70; N, 4.08%).

EXAMPLE 25

3-(3-Trifluoromethylphenyl)quinuclidine Hydrogen Oxalate 2,3-Dehydro-3-(3-trifluoromethylphenyl)quinuclidine (1.175 g, 4.6 mmol, Example 24) was hydrogenated at 3.5×10$^5$ N.m$^{-2}$ (50 psi) in ethanol (40 ML) containing 10% palladium on carbon (120 mg). The reaction mixture was filtered, than evaporated to dryness, then purified by column chromatography on silica using dichloromethane/methanol (20:1) to afford the title compound free base (0.93 g, 79%) as a yellow oil. The hydrogen oxalate salt had mp 122°–123° C. (propan-2-ol/methanol), R$_f$=0.19 in dichloromethane/methanol (5:1) on silica plates; $^1$H NMR (360 MHz, D$_2$O) δ 1.81–1.92 (2H, m) and 2.09–2.22 (2H, m, 5-CH$_2$ and 8-CH$_2$); 2.34–2.35 (1H, m, 4-CH); 3.28–3,47 (4H, m); 3.60–3.66 (2H, m) and 3.76–3.84 (1H, m, 2-CH$_2$, 3-CH, 6-CH$_2$ and 7-CH$_2$); 7.58–7.69 (4H, m, 4×Ar-H); MS, m/z 255 for M+ of free base. (Found: C, 55.53; H, 5.29; N, 4.08. C$_{14}$H$_{16}$F$_3$N.C$_2$H$_2$O$_4$ requires C, 55.65; H, 5.25; N, 4.06%).

EXAMPLE 26

3-(3,5-Dichlorophenyl)-3-hydroxyquinuclidine Oxalate

The title compound free base (1.40 g, 7%) was obtained from 3-quinuclidinone and 1-bromo-3,5-dichlorobenzene as described in Example 11. The hydrogen oxalate salt had mp>200° C. (dec) (propan-2-ol/methanol). R$_f$=0.25 in dichloromethane/methanol (4:1) on silica plates; $^1$H NMR (360 MHz, D$_2$O) δ 1.62–1.74 (1H, m); 1.95–2.01 (2H, m) and 2.36–2.46 (1H, m, 5-CH$_2$ and 8-CH$_2$); 2.58–2.62 (1H, m, 4-CH); 3.26–3.29 (2H, m) and 3.40–3.44 (2H, m 6-CH$_2$ and 7-CH$_2$); 3.51–3.57 (1H, m) and 3.89 (1H, d, J=13 Hz, 2-CH$_2$); 7.52–7.55 (3H, m, 3×Ar-H); MS, m/z (CI+) 272 for M+ of free base. (Found: C, 52.40; H, 5.34; N, 4.32. C$_{13}$H$_{15}$Cl$_2$NO.0.6 C$_2$H$_2$O$_4$ requires C, 52.29; H, 5.01; N, 4.29%).

EXAMPLE 27

3-(3-Chlorophenyl)-2,3-dehydroquinuclidine Hydrogen Oxalate

The title compound free base (0.418 g, 55%) was obtained from 3-(3-chlorophenyl)-3-hydroxyquinuclidine (as described in Example 33) by the method described in Example 15, except that the reaction mixture was heated at reflux for 60 hours. The hydrogen oxalate salt had mp 150°–151° C. (propan-2-ol/methanol). R$_f$=0.40 in dichloromethane/methanol (4:1) on silica plates; MS, m/z 219 for M+ of free base. (Found: C, 57.88; H, 5.21; N, 4.48. C$_{13}$H$_{14}$ClN.C$_2$H$_2$O$_4$ requires C, 58.16; H, 5.21; N, 4.52%.

EXAMPLE 28

6-Hydroxy-6-(3-methoxyphenyl)-1-azabicyclo[3.2.1]octane Hydrogen Oxalate

The title compound free base (3.12 g, 22%) was obtained from 1-azabicyclo[3.2.1]octan-6-one (7.90 g) and 3-bromoanisole (8.4 mL) as described in Example 11. The hydrogen oxalate salt had mp 133°–136° C. (propan-2-ol). R$_f$=0.17 in dichloromethane/methanol (5:1) on silica plates; $^1$H NMR (360 MHz, D$_2$O) δ 1.80–2.22 (4H, m, 3-CH$_2$ and 4-CH$_2$); 2.91–2.94 (1H, m, 5-CH); 3.35–3.75 (5H, m, 2-CH$_2$, 7-CH and 8-CH$_2$); 3.85 (3H, s, OCH$_3$); 4.17 (1H, d, J=13 Hz, 7-CH); 7.02 (1H, dd, J=2,8 Hz, Ar-H); 7.12–7.16 (2H, m, 2×Ar-H); 7.42 (1H, dd, J=8 Hz, Ar-H); MS, m/z 232 for (M-H)+ of free base. (Found: C, 58.51; H 6.53; N, 4.45. C$_{14}$H$_{19}$NO$_2$.C$_2$H$_2$O$_4$.0.25 H$_2$O requires C, 58.62; H, 6.61; N, 4.27%).

EXAMPLE 29

3-(2,3-Dimethoxyphenyl)-3-hydroxyquinuclidine Hydrogen Oxalate $^n$Butyllithium (100 mL of a 1.6 M solution in hexane) was added dropwise to a stirred, cooled (−10° C.) solution of 2,3-dimethoxybenzene (20.4 mL, 0.16 mol) in anhydrous diethyl ether (100 mL) under a nitrogen atmosphere, keeping the temperature below −5° C. After addition the mixture was stirred at 0° C. for 2 hours then cooled to −20° C. A solution of 3-quinuclidinone (20.0 g, 0.16 mol) in anhydrous diethyl ether (100 mL) was added dropwise keeping the temperature below −10° C. then after the addition the mixture was stirred at 0° C. for 2 hours then at room temperature for 3 hours. Saturated ammonium chloride solution (200 mL) was added and 2 M hydrochloric acid added to pH=4. The aqueous layer was separated, washed with diethyl ether (100 mL) then basified to pH=12 with 2 M sodium hydroxide solution and extracted with dichloromethane (3×100 mL). The combined organics were dried (sodium sulphate) then evaporated to give a yellow gum (17.89 g) which was triturated with diethyl ether (3×60 mL) to afford a cream solid (8.82 g, 21%), mp>105° C. (dec). The hydrogen oxalate salt had mp>110° C. (dec). $R_f$=0.15 in dichloromethane/methanol (5:1) on silica plates, MS, m/z 263 for M+ of free base. HRMS, Found: M+2.63.1530, $C_{15}H_{21}NO_3$ requires M, 263.1521.

EXAMPLE 30

2,3-Dehydro-3-(2,3-dimethoxyphenyl)quinuclidine Hydrogen Oxalate

The title compound free base (0.81 g, 10%) was obtained from 3-(2,3-dimethoxyphenyl)-3-hydroxyquinuclidine (as described in Example 29) by the method described in Example 15. The hydrogen oxalate salt had mp 187°–189° C. (propan-2-ol). $R_f$=0.22 in dichloromethane/methanol (9:1) on silica plates; $^1$H NMR (250 MHz, $D_2O$) δ 1.84–2.01 (2H, m) and 2.06–2.22 (2H, m, 5-$CH_2$ and 8-$CH_2$); 3.16–3.32 (2H, m, 6-$CH_2$); 3.37–3.39 (1H, m, 4-CH); 3.57–3.70 (2H, m, 8-$CH_2$); 3.80 (3H, s) and 3.91 (3H, s, 2×$OCH_3$); 6.90 (1H, s, 2-CH); 6.98 (1H, dd, J=2, 7 Hz, Ar-H); 7.18–7.25 (2H, m, 2×Ar-H); MS, m/z 245 for M+ of free base. (Found: C, 58.80; H, 6.28; N, 4.19. $C_{15}H_{19}NO_2.C_2H_2O_4.0.75$ $H_2O$ requires C, 58.53; H, 6.50; N, 4.02%).

EXAMPLE 31

6-(3-Methoxyphenyl)-1-azabicyclo[3.2.1]oct-6-ene Hydrogen Oxalate

The title compound free base (0.45 g, 22%) was obtained from 6-hydroxy-6-(3-methoxyphenyl)-1-azabicyclo[3.2.1]octane (as described in Example 28) by the method described in Example 15. The hydrogen oxalate salt had mp>100° C. (dec). MS, m/z 215 for M+ of free base. HRMS, Found: (M-H)+ 214.1180, $C_{14}H_{16}NO$ requires (M-H), 214.1232.

EXAMPLE 32

2,3-Dehydro-3-(3,5-dichlorophenyl)quinuclidine Hydrogen Oxalate

The title compound free base (0.67 g, 71%) was obtained from 3-(3,5-dichlorophenyl)-3-hydroxyquinuclidine (prepared as described in Example 26) by the method described in Example 15, except that the reaction mixture was heated under reflux for 2 weeks. The hydrogen oxalate salt had mp 182°–184° C. (propan-2-ol/methanol). $R_f$=0.48 in dichloromethane/methanol (4:1) on silica plates; $^1$H NMR (360 MHz, $D_2O$) δ 1.82–1.89 (2H, m) and 2.10–2.18 (2H, m, 5-$CH_2$ and 8-$CH_2$); 3.15–3.23 (2H, m, 6-$CH_2$); 3.56–3.67 (3H, m, 4-CH and 7-$CH_2$); 7.01 (1H, d, J=1.5 Hz, 2-CH); 7.55 (3H, s, 3×Ar-H); MS, m/z 253 for M+ of free base. (Found: C, 52.35; H, 4.34; N, 4.05; Cl, 20.63. $C_{13}H_{13}Cl_2N.C_2H_2O_4$ requires C, 52.34; H, 4.39; N, 4.07; Cl, 20.60%).

EXAMPLE 33

3-(3-Chlorophenyl)-3-hydroxyquinuclidine Hydrogen Oxalate

The title compound free base (0.925 g, 5%) was obtained from 3-quinuclidinone and 3-chlorobromobenzene as described for Example 11. The hydrogen oxalate salt had mp 194°–196° C. (propan-2-ol/methanol). $R_f$=0.17 in dichloromethane/methanol (3:1) on silica plates; MS, m/z 237 for M+ of free base.

EXAMPLE 34

Endo- and Exo-6-(3-methoxyphenyl)-1-azabicyclo[3.2.1]octane Hydrogen Oxalate 6-(3-Methoxyphenyl)-1azabicyclo[3.2.1]oct-6-ene (0.37 g. 1.7 mmol, Example 31) was hydrogenated at $3.5 \times 10^5$ $N.m^{-2}$ (50 psi) in ethanol (15 mL) containing 10% palladium on carbon (20 mg). The free base mixture of diasteromers was obtained as a colourless oil (0.088 g, 24%). The hydrogen oxalate salt (mixture of endo (85%) and exo (15%) had mp 105°–110° C. (propan-2-ol/diethyl ether). MS, m/z 218 for (M+H)+ of free base. (Found: C, 61.82; H, 6.84; N, 4.47. $C_{14}H_{19}NO.C_2H_2O_4$. 0.25 $H_2O$ requires C, 61.62; H, 6.95; N, 4.49%).

EXAMPLE 35

3-(2,3-Dimethylphenyl)quinuclidine Hydrogen Oxalate 2,3-Dehydro-3-(2,3-dimethoxyphenyl)quinuclidine (0.55 g, 0.0022 mol, Example 30) was hydrogenated at $3.5 \times 10^5$ $N.m^{-2}$ (50 psi) in ethanol (20 mL) containing 10% palladium on carbon (60 mg). The free base was obtained as a colourless gum (0.17 g, 31%). The hydrogen oxalate salt had mp 98°–102° C. (dec) (propan-2-ol/diethyl ether). $R_f$=0.25 in dichloromethane/methanol (5:1) on silica plates; $^1$H NMR (360 MHz, $D_2O$) δ 1.79–1.87 (1H, m) and 1.96–2.20 (3H, m, 5-$CH_2$ and 8-$CH_2$); 2.20–2.23 (1H, m, 4-CH); 3.27–3.48 (5H, m) and 3.77–3.84 (2H, m, 2-$CH_2$, 3-CH, 6-$CH_2$ and 7-$CH_2$); 3.83 (3H, s) and 3.90 (3H, s, 2×$OCH_3$); 7.06 (1H, d, J=8 Hz, Ar-H); 7.10 (1H, dd, J=1, 8 Hz, Ar-H); 7.24 (1H, dd, J=8, 8 Hz, Ar-H); MS, m/z 247 for M+ of free base. (Found: C, 57.86; H, 7.01; N, 4.19. $C_{15}H_{21}NO_2.C_2H_2O_4.H_2O$ requires C, 57.45; H, 7.09; N, 3.94%).

EXAMPLE 36

3-Hydroxy-3-(3,4-methylenedioxyphenyl)quinuclidine Hydrogen Oxalate

The title compound free base (12.0 g, 61%) was obtained from 3-quinuclidinone and 3,4-methylenedioxybromobenzene as described for Example 11. The hydrogen oxalate salt had mp 165°–166° C. (propan-2-ol/methanol). MS, m/z 247 for M+ of free base. (Found: C, 56.77; H, 5.89; N, 4.06. $C_{14}H_{17}NO_3.C_2H_2O_4$ requires C, 56.97; H, 5.67; N, 4.15%).

EXAMPLE 37

3-(3,5-Dichlorophenyl)quinuclidine Hydrogen Oxalate 2,3-Dehydro-3-(3,5-dichlorophenyl)quinuclidine (0.50 g, 1.97 mmol, Example 32) was hydrogenated at atmospheric pressure in ethanol (5 mL) containing platinum oxide (40 mg). The mixture was filtered then evaporated and the crude product purified by column chromatography on silica using dichloromethane/methanol (9:1) to afford the title compound free base as a colourless solid (34 mg, 7%). The hydrogen oxalate salt had mp 190°-192° C. (propan-2-ol). $R_f=0.25$ in dichloromethane/methanol (3:1) on silica plates; $^1$H NMR (360 MHz, D$_2$O) δ 1.82–1.88 (2H, m) and 2.08–2.14 (2H, m, 5-CH$_2$ and 8-CH$_2$); 2.31–2.32 (1H, m, 4-CH); 3.30–3.42 (4H, m) 6-CH$_2$ and 7-CH$_2$); 3.48–3.56 (2H, m, 2-CH$_2$); 3.75 (1H, ddd, $J_1=2$ Hz, $J_2=J_3=14$ Hz, 3-CH); 7.36 (2H, d, $J=2$ Hz, 2×Ar-H); 7.44 (1H, dd, $J_1=J_2=2$ Hz, Ar-H); MS, m/z 255 for M$^+$ of free base. (Found: C, 51.94; H, 4.98; N, 4.02. C$_{13}$H$_{15}$Cl$_2$N.C$_2$H$_2$O$_4$ requires C, 52.04; H, 4.95; N, 4.05%).

EXAMPLE 38

3-(3,5-Dimethoxyphenyl)-3-hydroxyquinuclidine Oxalate

The title compound free base (13.5 g, 64%) was obtained from 3-quinuclidinone and 3,5-dimethoxybromobenzene (M. R. Detty, B. J. Murry, *J. Amer. Chem. Soc.*, 1983, 105, 883–890) as described for Example 11. The oxalate salt had mp 250°-251° C. (propan-2-ol/methanol). $R_f=0.29$ in dichloromethane/methanol (19:1) on alumina plates; $^1$H NMR (360 MHz, D$_2$O) δ 1.66–1.77 (1H, m) 1.92–2.05 (2H, m) and 2.38–2.49 (1H, m, 5-CH$_2$ and 8-CH$_2$); 2.63–2.70 (1H, m, 4-CH); 3.12–3.52 (4H, m, 6-CH$_2$ and 7-CH$_2$); 3.56 (1H, dd, $J=2$, 14 Hz, one of 2-CH$_2$); 3.87 (6H, s, 2×OCH$_3$); 3.97 (1H, d, $J=14$ Hz, one of 2-CH$_2$); 6.65 (1H, dd, $J_1=J_2=2$ Hz, Ar-H); 6.74 (2H, d, $J=2$ Hz, 2×Ar-H); MS, m/z 263 for M$^+$ of free base. (Found: C, 61.72; H, 7.61; N, 4.68; C$_{15}$H$_{21}$NO$_3$.0.5 C$_2$H$_2$O$_4$.0.25 H$_2$O requires C, 61.43; H, 7.25; N, 4.48%).

EXAMPLE 39

2,3-Dehydro-3-(3,5-dimethoxyphenyl)quinuclidine Hydrogen Oxalate

The title compound free base (10 g, 86%) was obtained from 3-(3,5-dimethoxyphenyl)-3-hydroxyquinuclidine (as described in Example 38) by the method described in Example 15. The hydrogen oxalate salt had mp 140°-142° C. (propan-2-ol/diethyl ether). $R_f=0.22$ in dichloromethane/methanol (99:1) on alumina plates; $^1$H NMR (360 MHz, D$_2$O) δ 1.81–1.92 (2H, m) and 2.10–2.22 (2H, m 5-CH$_2$ and 8-CH$_2$); 3.12–3.25 (2H, m, 6-CH$_2$); 3.57–3.69 (3H, m, 4-CH and 7-CH$_2$); 3.86 (6H, s, 2×OCH$_3$); 6.66 (1H, dd, $J_1=J_2=2$ Hz, Ar-H); 6.76 (2H, d, $J=2$ Hz, 2××Ar-H); 6.98 (1H, s, 2-CH); MS, m/z 245 for M$^+$ of free base. (Found: C, 60.31; H, 6.31; N, 4.05. C$_{15}$H$_{19}$NO$_2$.C$_2$H$_2$O$_4$.0.25 H$_2$O requires C, 60.08; H, 6.38; N, 4.12%).

EXAMPLE 40

3-(3,5-Dimethoxyphenyl)quinuclidine Sesquioxalate 2,3-Dehydro-3-(3,5-dimethoxyphenyl)quinuclidine (9.5 g, 0.039 mmol, Example 39) was hydrogenated at 3.5×10$^5$ N.m$^{-2}$ (50 psi) in ethanol (90 mL) containing 10% palladium on carbon (1.9 g). The reaction mixture was filtered, evaporated to dryness, then purified by column chromatography on silica using dichloromethane/methanol (19:1) to afford the title compound free base as a colourless semi-solid (8.2 g, 86%). The sesquioxalate salt had mp 142°-145° C. (ethanol). $R_f=0.51$ in dichloromethane/methanol (19:1) on alumina plates; $^1$H NMR (360 MHz, D$_2$O) δ 1.75–2.22 (4H, m, 5-CH$_2$ and 8-CH$_2$); 2.24–2.31 (1H, m, 4-CH); 3.26–3.60 (5H, m), one of 2-CH$_2$, 6-CH$_2$ and 7-CH$_2$); 3.69–3.80 (2H, m, one of 2-CH$_2$ and 3-CH); 3.86 (6H, s, 2×OCH$_3$); 6.54 (1H, dd, $J_1=J_2=2$ Hz, Ar-H); 6.58 (2H, d, $J=2$ Hz, 2 ×Ar-H); MS, m/z 247 for M$^+$ of free base. (Found: C, 55.95; H, 6.42; N, 3.59. C$_{15}$H$_{21}$NO$_2$.1.5 C$_2$H$_2$O requires C, 55.88; H, 6.38; N, 3.62%).

EXAMPLE 41

3-(3,5-Bis-trifluoromethylphenyl)-3-hydroxyquinuclidine Hydrogen Oxalate

The title compound free base (4.2 g, 16%) was obtained from 3-quinuclidinone and 1-bromo-3,5-bistrifluoromethylbenzene as described for Example 11. The hydrogen oxalate salt had mp 173°-175° C. (propan-2-ol). $R_f=0.16$ dichloromethane/methanol (9.1) on silica plates. MS, m/z 340 for (M+H)$^+$ of free base. (Found: C, 47.60; H, 4.07; N, 3.29. C$_{15}$H$_{15}$NO.C$_2$H$_2$O$_4$ requires C, 47.56; H, 3.99; N, 3.26%).

EXAMPLE 42

3-(3,5-Bis-trifluoromethylphenyl)-2,3-dehydroquinuclidine Hydrogen Oxalate

The title compound free base (0.95 g, 33%) was obtained from 3-(3,5-bis-trifluoromethylphenyl)-3-hydroxyquinuclidine (as described in Example 41) by the method described in Example 15, except that the reaction mixture was heated at reflux for 7 days. The hydrogen oxalate salt had mp 205°-207° C. (propan-2-ol/methanol). $R_f=0.70$ in dichloromethane/methanol (9:1) on silica plates; $^1$H NMR (360 MHz, D$_2$O) δ 1.87–1.95 (2H, m) and 2.07–2.25 (2H, m 5-CH$_2$ and 8-CH$_2$); 3.18–3.29 (2H, m, 6-CH$_2$); 3.62–3.71 (3H, m, 4-CH and 7-CH$_2$); 7.16 (1H, d, $J=1.5$ Hz, 2-CH); 8.12–8.15 (3H, m, 3×ArH); MS, m/z 321 for M$^+$ of free base. (Found: C, 49.74; H, 3.54; N, 3.37. C$_{15}$H$_{13}$F$_6$N.C$_2$H$_2$O$_4$ requires C, 49.65; H, 3.68; N, 3.41%).

EXAMPLE 43

3-(3,5-Bis-trifluoromethylphenyl)quinuclidine Hydrogen Oxalate 3-(3,5-Bis-trifluoromethylphenyl)-2,3-dehydroquinuclidine (0.80 g, 2.5 mmol, Example 42) was hydrogenated at 3.5×10$^5$ N.m$^{-2}$ (50 psi) in ethanol (30 mL) containing 10% palladium on carbon (0.10 g). The hydrogen oxalate salt had mp 140°-142° C. (propan-2-ol). $R_f=0.20$ in dichloromethane/methanol (9:1) on silica plates; $^1$H NMR (360 MHz, D$_2$O) δ 1.83–1.88 (2H, m) and 2.11–2.21 (2H, m, 5-CH$_2$ and 8-CH$_2$); 2.14–2.42 (1H, m, 4-CH); 3.32–3.49 (4H, m, 6-CH$_2$ and 7-CH$_2$); 3.63–3.74 (2H, m) and 3.81–3.86 (1H, m, 2-CH$_2$ and 3-CH); 7.94 (2H, s, 2×Ar-H); 8.04 (1H, s, Ar-H). (Found: C, 49.38; H, 4.15; N, 3.32. C$_{15}$H$_{15}$F$_6$N.C$_2$H$_2$O$_4$ requires C, 49.40; H, 4.15; N, 3.38%).

EXAMPLE 44

2,3-Dehydro-3-(3,4-methylenedioxyphenyl)quinuclidine Hydrogen Oxalate

The title compound free base (1.05 g, 11%) was obtained from 3-hydroxy-3-(3,4-methylenedioxyphenyl)-quinuclidine (as described in Example 36) by the method described in Example 15, except that the reaction mixture was heated at reflux for 3 days. The hydrogen oxalate salt had mp 168°–170° C. (propan-2-ol/methanol). $R_f=0.30$ in dichloromethane/methanol (9:1) on silica plates; $^1$H NMR (360 MHz, D$_2$O) δ 1.81–1.89 (2H, m) and 2.10–2.19 (2H, m, 5-CH$_2$ and 8-CH$_2$); 3.13–3.22 (2H, m, 6-CH$_2$); 3.54–3.64 (3H, m, 4-CH and 7-CH$_2$); 6.02 (2s, OCH$_2$O); 6.86 (1H, d, J=1 Hz, 2-CH); 6.96 (1H, d, J=8 Hz, Ar-H); 7.09–7.14 (2H, m, 2×Ar-H); MS, m/z 230 for (M+H)$^+$ of free base. (Found: C, 59.54; H, 5.50; N, 4.27. C$_{14}$H$_{15}$NO$_2$.1.1 C$_2$H$_2$O$_4$ requires C, 59.27; H, 5.28; N, 4.27%).

EXAMPLE 45

3-Hydroxy-3-(3-methoxyphenyl)-1-azabicyclo[2.2.1]heptane Hydrogen Oxalate

The title compound free base (6.55 g, 37%) was obtained from 3-bromoanisole and 1-azabicyclo[2.2.1]heptan-3-one (*J.C.S. Chem. Commun.*, 1988, 1618–1619) as described in Example 11. The hydrogen oxalate salt had mp 152°–157° C. (propan-2-ol/methanol). MS, m/z 219 for M$^+$ of free base.

EXAMPLE 46

3-(3-Methoxyphenyl)-1-azabicyclo[2.2.1]hept-2-ene Hydrogen Oxalate

Thionyl chloride (0.82 mL, 11.2 mmol) was added to a stirred solution of 3-hydroxy-3-(3-methoxyphenyl)-1-azabicyclo[2.2.1]heptane (0.502 g, 2.25 mmol, Example 45) in anhydrous dichloromethane (30 mL). After stirring at room temperature for 1 hour the solution was heated under reflux for 30 minutes. The reaction mixture was cooled, water (20 mL) added followed by potassium carbonate (to pH~12) then the mixture was extracted with dichloromethane (3×50 mL). The combined organics were dried (sodium sulphate) then evaporated to dryness to give an oil (0.60 g). The product was purified by column chromatography on neutral alumina using methanol/ethyl acetate (gradient elution) to afford the title compound free base (0.11 g, 24%) as a pale brown oil. The hydrogen oxalate salt had mp 142°–146° C. (propan-2-ol/methanol/diethyl ether). MS, Cl$^+$, m/z 202 for (M+H)$^+$ of free base; $^1$H NMR (250 MHz, D$_2$O) δ 1.76–1.84 (1H, m) and 2.39–2.51 (1H, m, 5-CH$_2$); 3.20–3.30 (2H, m)3.82–3.92 (1H, m, 6-CH$_2$ and 7-CH$_2$); 3.86 (3H, s, OCH$_3$); 4.07 (1H, d, J=3 Hz, 4-CH); 7.00 (1H, s, 2-CH); 7.06–7.14 (2H, m, 2×Ar-H); 7.22 (1H, d, J=8 Hz, Ar-H); 7.44 (1H, dd, J$_1$=J$_2$=8 Hz, Ar-H).

EXAMPLE 47

Endo-3-(3-Methoxyphenyl)-1-azabicyclo[2.2.1]heptane Hydrogen Tartrate 3-(3-Methoxyphenyl)-1-azabicicylo[2.2.1]hept-2-ene (0.37 g, 1.84 mmol, Example 46) was hydrogenated at 3.5×10$^5$ N.m$^{-2}$ (50 psi) in methanol (120 mL) containing 10% palladium on carbon (0.211 g). The mixture was filtered and the filtrate evaporated to dryness to give a solid (0.36 g) which was purified by column chromatography on silica using dichloromethane/methanol/aqueous ammonia solution (70:30:2–4) to afford the title compound as an oil (0.271 g, 73%). $^1$H NMR (250 MHz, CDCl$_3$) δ 1.24–1.48 (2H, m, 5-CH$_2$); 2.48–2.94 (6H, m) and 3.16–3.40 (2H, m, 2-CH$_2$, 3-CH, 4-CH, 6-CH$_2$ and 7-CH$_2$); 3.80 (3H, s, OCH$_3$); 6.70–6.82 (3H, m, 3×Ar-H); 7.22 (1H, dd, J$_1$=J$_2$=8 Hz, Ar-H). The hydrogen tartrate salt had mp 145°–152° C. (ethanol). $^1$H NMR (250 MHz, D$_2$O) δ 1.58–1.74 (1H, m) and 1.85–2.04 (1H, m, 5-CH$_2$); 3.22–3.55 (6H, m) and 3.76–4.00 (2H, m, 2-CH$_2$, 3-CH, 4-CH, 6-CH$_2$ and 7-CH$_2$) overlapped with 3.85 (3H, s, OCH$_3$); 4.50 (2×CH of racemic tartaric acid); 6.88–7.00 (3H, m, 3×Ar-H); 7.41 (1H, dd, J$_1$=J$_2$=8 Hz, Ar-H); MS, m/z 203 for M$^+$ for free base. (Found: C, 57.57; H, 6.63; N, 3.81. C$_{13}$H$_{17}$NO.C$_4$H$_6$ O$_6$ requires C,57.78; H, 6.56; N, 3.96%).

PHARMACEUTICAL EXAMPLES

| | Amount-mg | | |
|---|---|---|---|
| 1. Tablets containing 1–25 mg of compound (1) | | | |
| Compound (1) | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |
| 2. Tablets containing 26–100 mg of compound (1) | | | |
| Compound (1) | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

Compound (1), lactose, and a portion of the corn starch are mixed together and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100.0 mg of compound (1) per tablet.

We claim:

1. A method for the treatment of neurological and mental disorders, which comprises the administration to a patient in need of such treatment a benzene compound of Formula I:

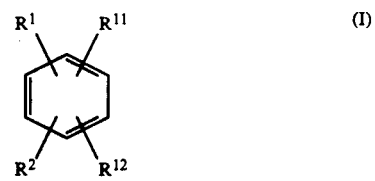

salt or prodrug thereof, substituted on one of the ring carbon atoms with a R$^1$ substituent selected from the group consisting of non-aromatic 1-azabicyclic and non-fused 1-azabicyclic ring system and independently substituted on each of the other ring carbon atoms with a R$^2$, R$^{11}$ and R$^{12}$ substituent selected from the group consisting of hydrogen, halo, —CF$_3$, OR$^6$, —NR$^6$R$^7$, —NHOR$^6$, —NHNH$_2$, —CN, COR$^8$, and substituted or unsubstituted, saturated or unsaturated hydrocarbon groups, provided that at least one of R$^2$, R$^{11}$ and R$^{12}$ is other than hydrogen or a hydrocarbon group, or R$^2$ and R$^{11}$ or R$^{12}$ taken together form a C$_{1-6}$ alkylenedioxy ring, wherein R$^6$ is selected from C$_{1-6}$ alkyl, C$_{2-6}$ alkenyl and C$_{2-6}$ alkynyl, wherein R$^7$ is selected from the group consisting of hydrogen, C$_{1-6}$ alkyl and —COCH$_3$, and R$^8$ is selected from the group consisting of OH, —OR$^6$, NHR$^7$ and —NR$^6$R$^7$.

2. The method according to claim 1 wherein, when R$^1$ is 3-hydroxy-quinuclidin-3-yl, and R$^{11}$ and R$^{12}$ are hydrogen, then R$^2$ is o- or p-methoxy, or p-chloro.

* * * * *